(12) United States Patent
Côté et al.

(10) Patent No.: US 6,210,922 B1
(45) Date of Patent: Apr. 3, 2001

(54) SERUM FREE PRODUCTION OF RECOMBINANT PROTEINS AND ADENOVIRAL VECTORS

(75) Inventors: M. T. Johanne Côté, Pierrefonds; Amine A. Kamen, Montréal; Bernard Massie, Laval, all of (CA)

(73) Assignee: National Research Council of Canada, Ottawa (CA)

( * ) Notice: Subject to any disclaimer, the term of this patent is extended or adjusted under 35 U.S.C. 154(b) by 0 days.

(21) Appl. No.: 09/201,168

(22) Filed: Nov. 30, 1998

(51) Int. Cl.⁷ .................................................. C12N 5/10
(52) U.S. Cl. .................. 435/69.1; 435/70.3; 435/366; 435/369; 435/455; 435/463
(58) Field of Search .................................... 435/325, 366, 435/369, 69.1, 70.3, 455, 463

(56) References Cited

FOREIGN PATENT DOCUMENTS

9822588 * 5/1998 (WO) .

OTHER PUBLICATIONS

Schoofs et al., Cytotechnology 28 (1–3): 81–89 (1998).*
Kyung et al., Cytotechnology 17(2): 109–115 (1995). Abstract.*
Grinnell et al., Blood 76(12): 2546–2554 (Dec. 15, 1990).*
Kim et al., Biotechnology Letters 16(6): 549–554 (Jun. 1994).*
Berg et al., BioTechniques 14(6): 972–978 (1993).*
Acsadi, G. et al. 1994. Hum. Mol. Genet. 3: 579–584.
Côté, J et al. 1998. Biotechnology and Bioengineering 59(5): 567–575.
Côté, J et al. 1997. Biotechnol. Prog. 13: 709–714.
Garnier, A et al. 1994. Cytotechnology 15: 145–155.
Kamen, A. A. et al. (1991) Biotech. Bioeng. 38 : 619–628.
Mosser D.D. et al. 1997. BioTechniques 22:150–161.
Nadeau, I et al. 1996 Biotech. Bioeng. 51: 613–623.
Peshwa, M.V et al. 1993 Biotech. Bioeng. 41: 179–187.
Trapnell, B.C. and Gorzilia, M. 1994 Curr. Opinion Biotechnol. 5: 617–625.

* cited by examiner

*Primary Examiner*—Jean C. Witz
(74) *Attorney, Agent, or Firm*—Swabey Ogilvy Renault; France Côté

(57) ABSTRACT

The present invention relates to a method of serum-free production of recombinant proteins and adenoviral vectors; cell lines viable in a serum-free medium and method of obtaining same.

12 Claims, 9 Drawing Sheets

SERUM FREE PRODUCTION OF RECOMBINANT PROTEINS AND ADENOVIRAL VECTORS

BACKGROUND OF THE INVENTION (a) Field of the Invention

The invention relates to a method of serum-free production of recombinant proteins and adenoviral vectors; cell lines viable in a serum-free medium and method of obtaining same.

(b) Description of Prior Art

The need for the production of recombinant proteins as well as viral particles able to mediate gene transfer and expression in vivo for gene therapy is constantly increasing. The use of recombinant adenovirus (AdV) in gene therapy as well as live viral vaccines has been extensively reported (Trapnell, B. C. and Gorzilia, M. 1994 Curr. Opinion Biotechnol. 5: 617–625). More recently, reported the use of AdV as vaccines for inducing specific T-cell immunity for cancer therapy. The transformed human embryonic kidney cell line 293 which constitutively express Ad5 E1A and E1B genes is used for its ability to support the replication of an E1A+E1B-defective adenoviral particle. These vectors are basically wild type human adenoviruses in which the E1A and E1B, the essential genes, have been deleted. These deletions, together with other less crucial ones, provide room in the capsid for recombinant genes and also prohibit the vector growth in normal cell lines.

The complementing human embryonic kidney 293 cell line and its derivatives which have been adapted to suspension culture, the 293S cells, will sustain the recombinant adenoviral vector replication. This cell line can be used for AdV production as well as for high level expression of r-proteins especially those for which activity is modulated by complex posttranslational modifications. Both types of product would benefit from the development of an effective serum-free medium (SFM) that would allow high cell growth rate and cell density as well as high yield of recombinant proteins and AdVs. The only serum-free formulations reported to support growth of 293 cells are proprietary in nature. Furthermore, doubling times ranging from 36 to 40 hours were much higher than doubling times of 18 to 22 hours measured in serum-containing media for single-cell suspension culture. There are, at present, no reports of adenoviral particle production by 293 cells in serum-free suspension culture.

The numerous problems associated with the presence of serum in culture medium are high cost, batch-to-batch variability, regulatory considerations and the difficulty in removing serum proteins when purifying the product of interest. These concerns are heightened when the final product is to be used as an injectable therapeutic. Considering this, one would expect that by now the adaptation of a cell line to SFM would be a routine laboratory work. However, since each cell line have it's very own growth and production characteristics, a universal SFM that would be efficient for all cell types does not yet exist. The multitude of commercial SFM formulations available assess the diversity of the needs. Furthermore, the literature often oversimplifies the development process of a SFM. Although, certain cell lines can be adapted spontaneously from serum-containing medium to SFM, a number of other cell lines need a sophisticated mixture of adaptation and screening steps in order to be weaned from serum-containing medium. This is especially true when more than one performance criteria has to be met. In practice, the development process usually involves: a) screening of media formulations, b) cell line adaptation following a blend of gradual or abrupt weaning steps, c) cell line cloning or sub-cloning in order to isolate better performing individual cells, and d) clone screening based on multiple performance criteria, namely cell growth rate, maximum cell density, resistance to agitation stress, lack of aggregate formation, and product yield. Since all the steps described above can rarely be performed in a simultaneous manner, empirical choices must be made during the development process that depend as much as on objective criteria as on a laboratory personnel experience and skills. To our knowledge, no universal method has been devised to address the SFM development process.

The large amount of viral particles required in gene therapy emphasizes the need for scale-up when possible. Suspension culture is often preferred to micro-carriers because of scale up and cost concerns. Testing of serum-free media is not trivial when the bioprocess involves infection of cells. The absence of serum in suspension culture leaves the shear-sensitive infected cells unprotected. The limited duration of the AdV production phase, 48 to 72 hours post infection when infected cells become fragile and might be subject to important cell lysis, may complicate the data analysis.

It would be highly desirable to be provided with a method of serum-free production of recombinant proteins and adenoviral vectors; cell lines viable in a serum-free medium and method of obtaining same.

SUMMARY OF THE INVENTION

One aim of the present invention is to provide a method of serum-free production of recombinant proteins and adenoviral vectors.

Another aim of the present invention is to provide cell lines viable in a serum-free medium.

Another aim of the present invention is to provide a method of obtaining cell lines viable in a serum-free medium.

In accordance with the present invention there is provided a serum-free medium viable cell line, which comprises an immortalized animal cell line for the expression of recombinant proteins and/or adenoviral vectors in a serum-free medium.

A preferred cell line of the present invention is a mammal cell line, or a human cell line, most preferably a human embryonic kidney cell line.

A preferred serum-free human embryonic kidney cell line in accordance with the present invention, which allows for the expression of recombinant adenoviral vectors, referred to as 293SF-3F6, has been deposited at the American Type Culture Collection (ATCC, 12301 Parklawn Drive, Rockville, Md. 20852 U.S.A.) on Sep. 25, 1998 under deposit number ATCC CRL-12585. This deposit is available to be public upon the grant of a patent to the assignee, National Research Council Canada, disclosing same. The deposit is also available as required by Foreign Patent laws in countries wherein counterpart applications are filed.

In accordance with the present invention there is provided with the use of the cell lines of the invention for establishing stable transfected cell line or for production of adenoviral vectors required for gene therapy.

In accordance with the present invention there is provided a method of serum-free production of recombinant proteins, which comprises the steps of:

a) transfecting a serum-free cell line of the invention with a cDNA coding for a recombinant protein to obtain transformants;

b) isolating a stable transformant of step a);
c) cultivating the isolated transformant of step b) in suspension in a serum-free medium to produce the recombinant proteins; and
d) isolating the recombinant proteins of step c).

The preferred recombinant protein may be selected from the group consisting of cytokines, G-protein coupled receptors, hormones and enzymes.

The step b) may be effected using a selection marker.

In accordance with the present invention there is provided a method of serum-free production of recombinant adenoviral vectors, which comprises the steps of:
a) transforming a serum-free cell line of the present invention, which is complementing defective of an adenoviral vector, with a recombinant adenoviral vector comprising a promoter operatively linked upstream to a marker gene and/or a therapeutic gene sequence relative to the direction of transcription in an adenoviral vector, wherein the promoter is controlling transcription of the marker gene and/or the therapeutic gene, wherein the cell line is complementing the recombinant adenoviral vector;
b) isolating a stable cell line of step a) using the marker; and
c) cultivating the isolated cells of step b) in suspension in a serum-free medium to produce the recombinant adenoviral vector.

The marker may be selected from the group consisting of green fluorescent protein, β-galactosidase or luciferase.

The vector of step a) includes, without limitation, Ad5 CMV-LacZ wherein LacZ gene is replaced by S65T GFP mutant gene, thereby having an increased emission signal intensity detectable in single cells by fluorescent microscopy or FCM In accordance with the present invention there is provided a method of obtaining cell lines for the expression of recombinant proteins and/or adenoviral vectors and which are viable in a serum-free medium, which comprises the steps of:
a) incubating immortalized cells secreting recombinant proteins and/or adenoviral vectors in a serum-free medium and comparing production of recombinant proteins and/or adenoviral vectors as compared to serum-containing medium;
b) gradually adapting the immortalized serum-free cells of step a) to a low-calcium version of the serum-free medium, thereby reducing cell aggregation; and
c) screening and cloning cells of step b) based on their ability to grow in a serum-free medium at a rate and an extent comparable to parental cells in serum-containing medium as single cells.

The cells of step c) may be screened for their ability to grow at the highest specific cell growth rate and cell density while forming least and smallest cell aggregates in shake flask suspension culture.

For the purpose of the present invention the following terms are defined below.

The term "cell line" is intended to mean any cell line which may be used in accordance with the present invention for the expression of recombinant proteins and/or adenoviral vectors. Such cell lines may be already immortalized or may be rendered immortalized prior to their modification to become viable in a serum-free medium. Preferably, the cell line are of animal origin, such as mammal origin, and more preferably of human origin. Preferred cell lines include, without limitation, A-549, PER.C6, Jurkat, Namalwa, Hela and 293.

The term "serum-free medium" is intended to mean any medium which do not require the addition of animal serum. Such serum-free medium includes any basal formulation containing protein factors (which may be animal-derived) which does not require serum to support cellular function.

For the purpose of the present invention the following abbreviations are defined below.

| | |
|---|---|
| AdV | adenovirus vector; |
| Ad-GFP | recombinant adenovirus expressing a green fluorescent protein; |
| BCS | bovine calf serum; |
| BSA | bovine serum albumin; |
| CFDMEM | calcium-free DMEM; |
| CLC-SFM | complete LC-SFM; |
| DMSO | dimethylsulfoxide; |
| HFC | high-fluorescence cell; |
| hpi | hour post-infection; |
| IVP | infectious viral particle; |
| LC-SFM | low-calcium serum-free medium; |
| LFC | low-fluorescence cell; |
| FC | fluorescent cell; |
| FCM | flow cytometry; |
| MOI | multiplicity of infection; |
| r-protein | recombinant protein; |
| sEGFr | soluble epidermal growth factor receptor; and |
| SFM | serum-free medium. |

DETAILED DESCRIPTION OF THE INVENTION

In accordance with the present invention, there is provided the step-wise approach undertaken to select a serum-free medium (SFM) for the efficient production of a recombinant adenoviral vectors expressing β-galactosidase (Ad5 CMV-LacZ), in, for example, the complementing human embryonic kidney 293S cells. The cell line 293S is used herein to illustrate the cell line which can be used in accordance with the present invention rather than to limit the scope of the present invention.

Other cell line may be used in accordance with the present invention, including, without limitation, animal cells, mammalian cells and insect cells.

According to one embodiment of the present invention, in the first step, a 293S-derived transfectoma, secreting a soluble epidermal growth factor receptor sEGFr (D2-22), is used to estimate the potential of selected serum-free formulations to support the production of a recombinant protein as compared to serum-containing medium. Assays showed that only one among six commercial serum-free formulations could support both sEGFr production and cell growth in static or suspension culture. In commercially available calcium-containing serum-free formulations, the cell aggregates reached up to 3 mm in diameter. In the second step, 293S cells are gradually adapted to a low-calcium version of the selected medium (LC-SFM). Cells are cloned, and screened according to their ability to grow at a rate and an extent comparable to parental cells in serum-containing medium (standard) as single cells or small aggregates. The 293SF-3F6 clone, first adapted to and then cloned in the selected serum-free medium, is selected for further experiments. Bioreactor run performed with the 293SF-3F6 clone showed similar growth curve as in the shake flask controls. In the final step, the recombinant viral vector productivity of the 293S cells and the 293SF-3F6 clone is tested. The 293SF-3F6 cells infected by Ad5 CMV-LacZ in 3 L scale bioreactor maintained the specific productivities of both β-galactosidase and adenoviral vector equivalent to the shake flask controls in suspension culture. Results from this study clearly demonstrate that the 293SF-3F6 cell line thus selected may be used either for establishing stable transfected cell line or for the production of adenoviral vectors required for gene therapy studies.

The screening of serum-free media is done employing a transformed-293S cell line D2-22 which expresses the soluble epidermal growth factor receptor (sEGRr) instead of 293-AdV system. In shake flask suspension culture, the D2-22 clone is grown in serum-containing medium and showed a growth profile similar to the parent 293S cells.

This D2-22 cell line is used to compare the production potential of stable 293 cell-derived clones in serum-containing medium with commercial serum-free formulations. The best serum-free medium is selected based on the highest D2-22 cell growth rate, the maximum cell density achievable in batch culture, and sEGFr production levels over at least 30 days in culture. A low-calcium version of the selected SFM, LC-SFM, is then used to grow 293S cells in order to reduce cell aggregation. After complete adaptation of 293S cells to LC-SFM, the subpopulation 293SF is cloned twice and the 293SF-3F6 clone is picked up for its ability to grow at the highest specific cell growth rate and cell density while forming the least and the smallest cell aggregates in shake flask suspension culture.

Serum effect on intracellular viral replication or virus attachment to the cell membrane during infection process is not documented in the prevailing literature. Preliminary experiments in shake flasks are performed to assess AdV production in SFM. In the final step, the possibility of scale-up in the bioreactor is confirmed for serum-free suspension culture of 293SF-3F6 cells as well as AdV production in such conditions.

MATERIAL AND METHODS

Cell Lines and Recombinant Viral Vectors

The 293S cells, adapted to grow in suspension, were kindly provided by Dr. M. Matthew (Cold Spring Harbor Laboratories, Cold Spring Harbor, N.Y.). The D2-22 transfectoma derived from 293S and expressing the soluble epidermal growth factor receptor (sEGFr) was kindly provided by Dr. P. Jolicoeur. HeLa S3 cells were obtained from the ATCC (CCL 2.2; Rockville, Md.). The adenoviral vector, recombinant human adenovirus type 5 expressing the β-galactosidase under the control of the early promoter of cytomegalovirus, Ad5 CMV-LacZ (Acsadi, G. et al. 1994. Hum. Mol. Genet. 3:579–584), was used in this study. Viral stock aliquots were stored at –80° C. The 293SF cells were derived from the 293S cells after adaptation to growth in low-calcium serum-free medium (LC-SFM). The 293SF-3F6 sub-clone was obtained after two consecutive cloning steps by end-point dilution of 293SF cells with LC-SFM in 96-well plates.

Culture Media

The 293S cells were grown in calcium-free DMEM (CFDMEM, custom-made; American Bioorganics Inc., Niagara Falls, N.Y.) supplemented with 5% (v/v) COSMIC Bovine Calf Serum™ (Hyclone, Logan, Utah) and 0.1% (w/v) Pluronic F68 (GIBCO, Grand Island, N.Y.) as described previously (Garnier, A et al. 1994. Cytotechnology 15:145–155; Nadeau, I et al. 1996 Biotech. Bioeng. 51:613–623). HeLa S3 cells were grown in static culture in DMEM supplemented with 10% FBS (GIBCO). The commercial H-SFM developed for hybridoma culture and custom-made low-calcium H-SFM (LC-SFM) were bought from GIBCO. The 293SF cells grew readily in LC-SFM static culture but were more difficult to grow in suspension culture when seeding cell density was lower than $3 \times 10^5$ cells/mL. In order to improve cell viability in suspension, LC-SFM was supplemented with 0.1% (w/v) Bovine Serum Albumin (BSA #A7030; Sigma, St-Louis, Mo.) and 1% (v/v) chemically defined lipids (GIBCO) to get the complete LC-SFM (CLC-SFM). No additional Pluronic F68 was added to CLC-SFM since the chemically defined lipids are prepared in 10% (w/v) Pluronic F68. Bioreactor runs were performed with LC-SFM supplemented with 0.1% (w/v) BSA (BOVUMINAR #3410; INTERGEN, Purchase, N.Y.) and 0.1% (v/v) lipids (L-5146, Sigma, St-Louis, Mo.) and 0.1% (w/v) Pluronic F68 to grow 293SF cells in CLC-SFM.

Serum-free Cell Freezing and Thawing

Exponentially growing cells at a cell density lower than $8 \times 10^5$ cells/mL, were centrifuged and resuspended in cold, CLC-SFM containing 10% (v/v) DMSO (Sigma, St-Louis, Mo.) and then frozen at –80° C. The cell vials were transferred into liquid nitrogen for storage periods longer than 8 weeks. Cells were recovered by fast thawing at 37° C., followed by a 10-fold dilution in warm CLC-SFM and a 10 min. centrifugation at 200×g. After discarding the supernatant, the cell pellet was resuspended by gentle agitation and then fresh medium was added. The cell density was adjusted to no less than $3\times10^5$ cells/mL. Cell viability after thawing was usually higher than 80%. Cells were maintained in static culture for the first 48 hours before transferring to a shake flask for further cultivation.

Suspension Culture and Infection

Cells were maintained in suspension in 10 to 50 mL cultures in 50 to 250 mL glass shake flasks agitated at 110 rpm with an orbit length of 3.2 cm using an AROS 160 shaker (Barnstead/Thermolyne Corp., Ste-Therese, QC, Canada) in a 5% $CO_2$ incubator (FORMA Scientific, Marietta, Ohio) at 37° C. The D2-22 cells were cultured in 50 mL shake flasks with culture volume of 10 to 12 mL. The 293SF-3F6 clone and 293S cells were grown in their respective complete media (Table I) up to 35 mL in a 125 mL polycarbonate shake flask (CORNING, N.Y.).

TABLE I

| Conditions | Medium used | Cells | Medium renewal at 24 hpi | Glucose addition at 24 hpi |
|---|---|---|---|---|
| A | CFDMEM | 293S | NO | NO |
| B | CFDMEM | 293S | NO | YES |
| C | CLC-SFM 1X | 293SF-3F6 | NO | NO |
| D | CLC-SFM 1X | 293SF-3F6 | YES | NO |
| E | CLC-SFM 2X | 293SF-3F6 | NO | NO |
| F | CLC-SFM 2X | 293SF-3F6 | NO | YES |

Conditions tested in shake flask with infected cells. Medium was changed at 0 hpi in all conditions. Medium used referred to complete media as described in text.

The cells tended to form loosen aggregates of 2–12 cells, especially at cell densities higher than $1\times10^6$ cells/mL. During cell maintenance, cultures were kept in exponential phase by diluting cells approximately every second day in order to maintain cell densities between $1\times10^5$ cells/mL and $12\times10^5$ cells/mL. For infection experiments, exponentially growing cells were centrifuged and resuspended in fresh culture media at a cell density of $1\times10^6$ cells/mL. Infection was initiated by adding concentrated Ad5 CMV-LacZ to the cultures at a multiplicity of infection (MOI) of 10 (10 infectious viral particles, IVP per cell). A 500 µL cell suspension aliquot was transferred in sterile tubes at about 0, 24, 36, 48 and 72 hours post infection (hpi). Another 500 µL aliquot was placed in Eppendorf tubes and centrifuged at 500×g for 2 min (Savant Instruments Inc., Hicksville, N.Y.). The total-suspension samples and centrifugation supernatants were stored at −80° C. for further analyses. Adenoviral particles were recovered from the frozen total-suspension samples by 3 freeze-thaw cycles.

Cell Counts

A 300 µL culture aliquot was placed in a 6 mL polystyrene tube and agitated in order to break the cell clumps without affecting cell viability. This procedure was validated by evaluating cell viability by erythrosin B stain before and after the agitation as described by Garnier, A et al. 1994. Cytotechnology 15:145–155. No loss of viability was observed for cells grown in serum-containing medium. However, in LC-SFM, mortality due to this agitation was significant. There were large discrepancies in viability estimates obtained before and after de-clumping in samples from cultures done in CLC-SFM. Therefore, because of the low precision of the pre-agitation counts and the lower apparent viability post-agitation, we have chosen here to report total cell densities. The infection induced a cytopathic effect that resulted in single cell suspensions rendering cell de-clumping unnecessary and consequently cell viabilities more reliable.

Glucose Analyses

Sample glucose concentration was immediately measured off-line using a Companion™ 2 blood glucose sensor (MEDISENSE, Waltham, Mass.) and samples were frozen for further HPLC analyses (Garnier, A et al. 1994. Cytotechnology 15:145–155).

sEGFr Quantitation and β-galactosidase Activity Measurement

The active form of the sEGRr was quantified using a standard ELISA as described by Côté, J et al. (1998. Biotechnology and Bioengineering 59(5):567–575). The standard deviation for replicates was lower than 15%. The β-galactosidase activity in the cell lysate was determined by a standard colorimetric assay using ONPG as the substrate (Côté, J et al. 1998. Biotechnology and Bioengineering 59(5):567–575). The factor used for converting absorbance readings to β-galactosidase activity was calculated using the equation of Wickham et al. (1992).

Ad5 CMV-LacZ Titer Estimation with HeLa S3 or 293S Cells

For AdV titration, HeLa S3 cells were chosen over 293 cells because they do not allow adenoviral replication but can still express recombinant protein when infected by an AdV (Persson et al. 1983). This particularity was used to evaluate the virus titer in samples at low MOI and low cell density ($3\times10^5$ cells/mL). AdVs were released from 293-total-suspension samples taken between 2 and 72 hpi by three freeze-thaw cycles. HeLa S3 cells were seeded at $1\times10^6$ cells per well in 6-well plates. One mL of diluted AdV sample was added to each well, giving a final volume of 3 mL per well. The β-galactosidase expressed by infected HeLa S3 cells at 48 hpi was recovered from total well samples by 3 freeze-thaw cycles and analyzed as described above. The β-galactosidase activity measured in HeLa S3 cells increased linearly with the volume of AdV sample added. So, the β-galactosidase activity measured in HeLa S3 cells was appropriate and related to the amount of AdV produced either by infected 293S or 293SF-3F6 cell cultures. The 293S cells were also used for AdV titration. The 6-well plates containing $1\times10^6$ 293S cells in 1.5 mL per well were incubated for 16–18 hours and then β-galactosidase recovered by 3 freeze-thaw cycles was measured as described above. In the short post-infection incubation period, AdV replication cycle is not yet complete. During the same period, the β-galactosidase was expressed at a level that was measurable by enzymatic assay. Using the 293S cells with a short incubation period allowed faster estimation of sample AdV.

Bioreactor

Inoculum for bioreactor runs were prepared using up to 600 mL of culture in 2000 mL glass shake flasks on a FORMA orbital shaker at 130 rpm and 37° C. (FORMA Scientific, Marietta, Ohio). These large culture volumes were operated with closed cap in absence of additional $CO_2$. The $1.2\times10^8$ cells inoculated in the 2000 mL-shake flask produce sufficient amount of $CO_2$ to maintain the pH at 7. The exponentially growing cell inoculum was diluted with fresh medium prior to inoculation.

A 3-L Chemap CF-2000 bioreactor (Mannedorf, Switzerland) equipped with a helical-ribbon impeller (HRI) was used to improve gas transfer (Kamen, A. A. et al. (1991) Biotech. Bioeng. 38:619–628) and to provide better mixing for 293SF-3F6 cultures. The agitation speed was maintained at 100 rpm for the first 60 hours and then increased to 120 rpm after huge cell aggregates of approximately 200 cells were observed. The pH was controlled at 7.2 since preliminary studies in shake flasks showed that increased pH was associated with reduced aggregation of 293SF-3F6 cell suspension culture. The pH was controlled by $CO_2$ in aeration gas-mixture and $NaHCO_3$ 7.5% (w/v). The dissolved oxygen was controlled at 40% air saturation using computer-coupled mass-flow controllers and FIX MMI software (Intellution, Mass.).

Two bioreactor runs were performed with 293SF-3F6 in CLC-SFM. The first one was done to assess the potential for cell growth and the second one for AdV production. The 293SF-3F6 cells were inoculated at about $2\times10^5$ cells/mL for both bioreactor runs. The working volume was 2.8 L. Batch culture was followed over 10 days for the first 293SF-3F6 run. The second bioreactor was harvested when cell density reached $8\times10^5$ cells/mL and infection was initiated by adding concentrated Ad5 CMV-LacZ in order to get an MOI of 10 at a cell density of $1\times10^7$ cells/mL for one hour. The volume was increased up to 2.8 L with fresh medium just before cells were transferred into the bioreactor. This concentration step was done to improve viral/cell interaction in order to achieve synchronous infection.

RESULTS AND DISCUSSION

D2-22 Cell Growth and sEGFr Production in Serum-containing Medium

Figure 1:
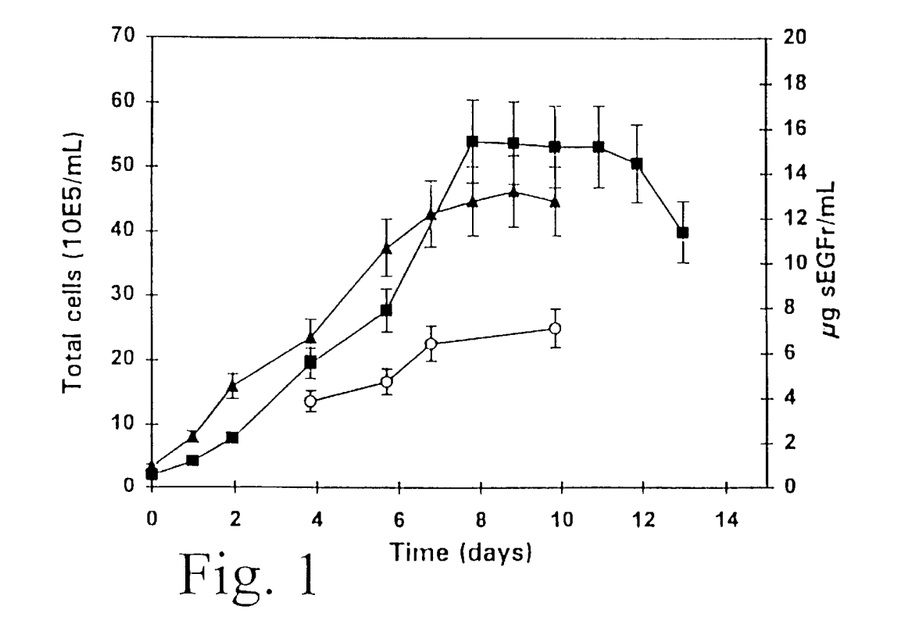
FIG. 1 illustrates sEGFr production (open circles) and comparative growth batch curves of 10 mL culture of D2-22 cells (closed triangles) and 293S cells (closed squares) in calcium-free DMEM supplemented with 5% (v/v) BCS and 0.1% (w/v) Pluronic F68 in 50 mL shake flasks.

Growth of 293S and D2-22 cells (293S-derived transfectoma secreting sEGFr) was first examined in 50 ml-shake flasks containing 10 mL CFDMEM supplemented with 5% BCS and 0.1% Pluronic F68. The growth curves of D2-22 cells and the parent 293S cells were similar, both cell lines reaching maximum densities between $4\times10^6$ and $5\times10^6$ cells/mL (FIG. 1). Typically, an exponential growth phase during the first days of culture was followed by a linear growth phase starting at day 2 or 3, at which time cell densities were higher than $1.5\times10^6$ to $2.0\times10^6$ cells/mL, and a plateau phase after 7 days. In some cultures the cells attached to the shake flask at the liquid/gas interface forming a ring-shape deposit and leading to an underestimation of the total number of cells in the flask. The problem could not be overcome by coating the shake flasks with silicone. The maximum production of sEGFr (7 $\mu$g/mL) was obtained by the time the cells reach the plateau. These sEGFr production levels were similar to what was obtained in static culture in identical conditions.

D2-22 Cell Adaptation to Serum-free Medium

The growth rate, maximum cell density in batch culture, and sEGFr production level of D2-22 cells were measured over many generations, when possible, in six serum-free media that were either commercial formulations or non-proprietary formulation amended with commercial supplements. The cells were diluted at least twice in each of the formulations tested prior to batch static culture. Many formulations did not sustain cell growth while others supported much lower cell growth rate and lower sEGFr productivity than serum-containing medium control. After two weeks of adaptation while cells were diluted when necessary in order to maintain cell density between $3\times10^5$ cells/mL and $10\times10^5$ cells/mL, usually every second or third day, the D2-22 cells recovered and grew well in static culture with a doubling time of about 22 hours in H-SFM. Although the cells were diluted at least twice a week, they began to form colonies that were tightly attached to the T-flask. At the beginning of the third week, in order to test the adaptability of these cells to serum-free suspension culture, part of the cell population was transferred into a shake flask under conditions described in Materials and Methods. The cells were inoculated at about $3\times10^5$ cells/mL and within minutes, cell aggregation was observed. It is well known that the calcium content of the culture medium may affect cellular adhesion. Peshwa et al. (Peshwa, M. V et al. 1993 Biotech. Bioeng. 41:179–187) reported that calcium concentrations ranging from 100 $\mu$M to 1 mM lead to 293 cell aggregation. Two serum-containing media commonly used for 293S suspension culture are JOKLIK medium (a calcium-free modification of MEM) and calcium-free DMEM. These, so-called, "calcium-free" media contain in fact trace amounts of calcium (approx. 10 $\mu$M) derived from the serum. These amounts are sufficient to support cell growth without promoting cell clumping. However, no calcium- and serum-free media were commercially available. In suspension culture, the calcium present in the original H-SFM formulation induced the formation of large clumps reaching a diameter of up to 3 mm. Although it was not possible to count cells in H-SFM, supernatant samples were analyzed for sEGFr. Amount of sEGFr obtained in H-SFM was similar than in serum-containing medium while much lower productions were achieved in other formulations or even no growth at all.

Adaptation of 293S Cells to LC-SFM

Figure 2:
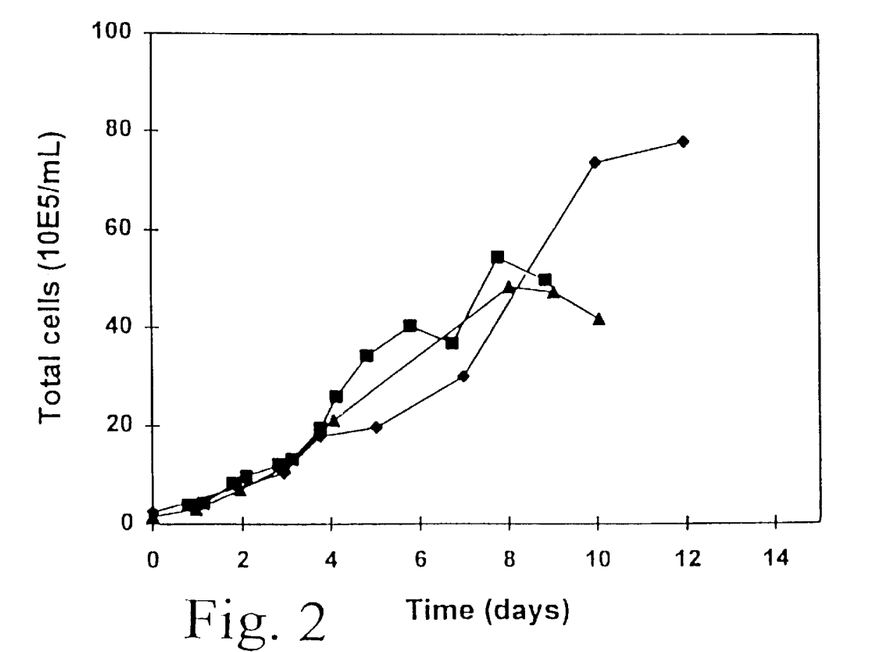
FIG. 2 illustrates 12 mL culture growth curves of 293S (triangles), 293SF-pool (squares) and 293SF-3F6 (diamonds) cells in 50 mL shake flasks containing their respective complete culture media.

In order to address the cell aggregation problems, custom made $CaCl_2$-free H-SFM formulation containing only 4 $\mu$M calcium was ordered from GIBCO (LC-SFM). This formulation supported serum-free growth of 293S in suspension and led to reduced cell aggregate size, especially at cell densities lower than $2\times10^6$ cells/mL. The 293S cells growing in CFDMEM with 5% BCS and 0.1% F68 were transferred into LC-SFM supplemented with 1% BCS. Since cell growth after two weeks in this formulation was adequate, another weaning step was achieved by complete BCS removal. Adaptation to unsupplemented LC-SFM was done in static culture prior to suspension culture. LC-SFM alone supported the growth of 293S cells in static culture and the adapted cell population was identified as 293SF-pool. In order to improve the cell viability in agitated culture BSA and lipids were added to LC-SFM (see Materials and Methods). This new formulation is referred to as complete LC-SFM (CLC-SFM). The 293SF-pool was cloned by end-point dilution in 96 well-plates using CLC-SFM. Different phenotypes were observed among all the clones. Many clones were picked based principally on their shapes and the clone exhibiting the best growth and smallest aggregates in suspension in CLC-SFM was selected for recloning. One of the best clone resulting from this process is referred to as 293SF-3F6. Batch culture growth curves of 293S in complete CFDMEM, and of 293SF-pool and 293SF-3F6 in CLC-SFM are presented in FIG. 2. The 293SF-pool and the parent 293S cells grew approximately at the same rate and reached similar plateau (approximately $5\times10^6$ cells/mL). The 293SF-3F6 clone had an overall growth rate similar to 293S and 293SF cell populations, but reached a significantly higher maximum cell density ($8\times10^6$ cells/mL) than 293S cells in batch culture. It has to be noticed that the 293S or 293SF cells did not grow that much in the same SFM formulation. The clone selection was then of the first importance for that improvement. The fact that the 293S cells did not secreted any recombinant protein or did not contain any gene that could be used for selection did complicate the overall clone selection during the cloning process. The selection criteria based on the cell population phenotype necessitated more effort than only adding selective agent in the culture medium or screening for the product secretion as it is usually done in cell culture cloning.

Infection Trials using 293SF-3F6 in CLC-SFM

The best r-protein production in the adenovirus-293S system is obtained when cells are infected at about $1\times10^6$ cells/mL in complete CFDMEM when the culture medium is renewed at infection (Garnier, A et al. 1994. Cytotechnology 15:145–155). In previous work, lactate level at infection or glutamine depletion at 48 hpi were reported to be responsible for the decrease of phosphate tyrosine phosphatase 1C production (Nadeau, I et al. 1996 Biotech. Bioeng. 51: 613–623). Optimal conditions (i.e. physiological pH) should be provided in order to maintain mammalian metabolic activities. Acidification may cause a decrease in the rates at which key nutrients are metabolized. Changing the culture medium at the time of infection decreases the lactic acid concentration and therefore re-establishes the initial culture conditions (pH, osmolality, etc.). This simple procedure was adopted for comparing product yields in 293S and 293SF-3F6 cells.

Specific productions of r-protein and AdV in 293S and 293SF-3F6 cells were compared together with environmental factors in the experimental design summarized in Table I. In order to identify any limitation due to the medium, a concentrated CLC-SFM formulation (CLC-SFM2x) was put to trial. This formulation contained twice the normal levels of amino acids, vitamins, and other proprietary LC-SFM components while the concentrations of the remaining components were unchanged. The osmolality of the concentrated medium was adjusted to 320 mOsm (comparable to regular CLC-SFM). The 293S cells in complete CFDMEM (condition A, Table I) were used as positive control.

Figure 3A:
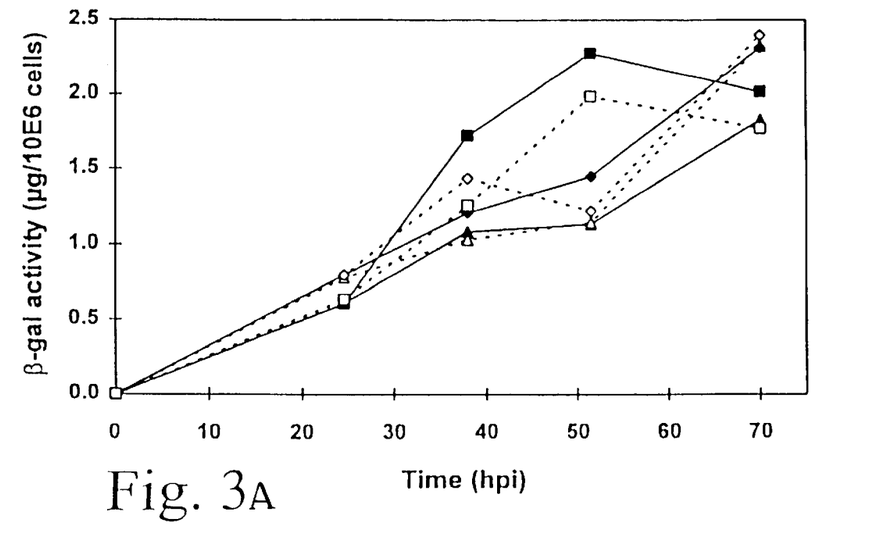
FIG. 3A illustrates comparative specific β-galactosidase production relative to IVPs produced by 35 mL culture of 293S cells in 125 mL shake flasks.

FIG. 3A represents the specific β-galactosidase production of 293S cells infected with Ad5 CMV-LacZ in complete CFDMEM and 293SF-3F6 cells in CLC-SFM. 293S cells were cultured in complete CFDMEM and 293SF-3F6 cells in CLC-SFM (see Table I for details) and all the cultures were infected at a cell density of 1×10$^6$ cells per mL. The maximum specific production was attained sooner in CLC-SFM 2x than in the other media (48 hpi instead of 72 hpi) even though, none of the measured nutrients had been completely depleted in any of the CLC-SFM cultures. One possible explanation is that a nutrient other than the ones measured was limiting. Another explanation is that a key nutrient is not completely depleted but is still limiting because the enzyme mainly metabolizing this component has a low affinity for its substrate (high $K_M$).

Production of infectious adenoviral particles was estimated by infecting HeLa S3 cells with Ad5 CMV-LacZ in wells as described in Materials and Methods and reported as infectious viral particles (IVPs) relative to 293S control. Dilutions were done in order to obtain absorbance values within the linear response range of the method. This linear response reflects a one virion per infected cell ratio (Côté, J et al. 1997. Biotechnol. Prog. 13:709–714) when cells are infected at low MOI. Because, the cell density is low in wells, the amount of β-galactosidase expressed should be limited only by the number of infectious viral particles present per well and not by limiting nutrients or inhibitory byproducts. One β-galactosidase activity unit is correlated to one IVP that expressed measurable β-galactosidase activity under standard conditions described above.

Figure 3B:
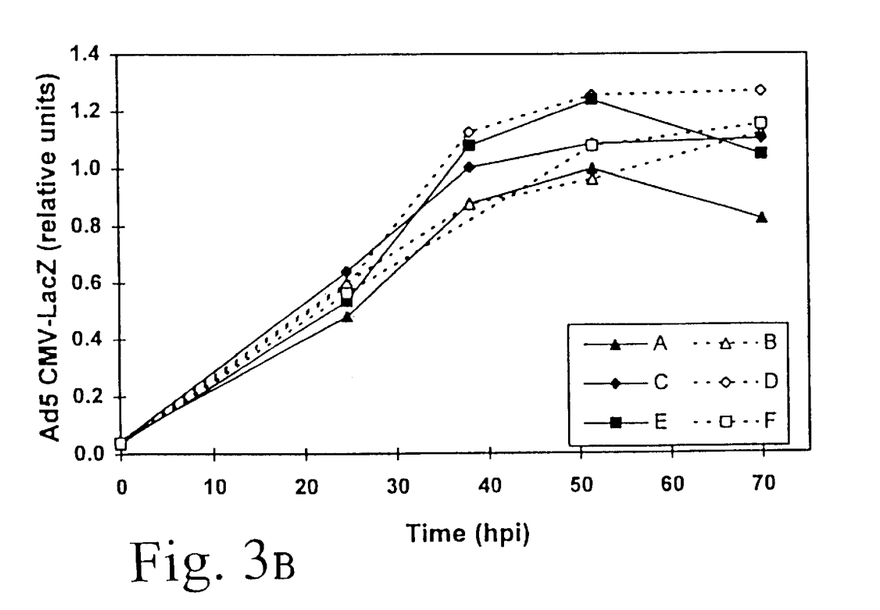
FIG. 3B illustrates comparative specific infectious Ad5 CMV-LacZ viral particles (IVPs) relative to IVPs produced by 35 mL culture of 293S cells in 125 mL shake flasks.

Relative infectious viral particle titers are reported on FIG. 3B. The values are relative to infectious adenoviral particle counts at 48 hpi for 293S cells in condition A where the medium was replaced at the time of infection only. Only the IVP fraction of the total AdVs released from total suspension samples were reported here. Maximum yield of IVP was improved by 20% in CLC-SFM 2x at 48 hpi. An important result is the apparent stability in culture of the infectious viral particles observed from 48 to 72 hpi for all the conditions where the medium was amended with glucose/EAA or replaced with fresh medium following centrifugation at 24 hpi (FIG. 3B, conditions B, D and F). Slight decreases in IVPs between 48 and 72 hpi was observed for conditions A and E where no nutrients additions were made to the cultures following infection whereas this tendency was not observed under condition C for unknown reasons.

The maximum final specific IVPs, at 72 hpi, varied form 1.1 for condition B to 1.3 for condition D suggesting that nutrient supplementation, or pH control, is necessary to maintain high AdV titer. Per cell IVP production levels, based on total cell counts, in the serum-free conditions appeared to be at least as high as those reached in serum-containing conditions. This is encouraging since other results using the Ad-GFP vector (Côté, J et al. 1997. Biotechnol. Prog. 13:709–714) showed that viability decreased faster in serum-free than in serum-containing conditions. Those results suggested that only cells that were still viable between 24 and 48 hpi were in fact participating in the IVP production. The fact that 293S and 293SF culture viabilities are comparable with Ad5 CMV-LacZ vector may indicate that 293SF-3F6 cells can sustain high viral production but might be more or less sensitive to high MOI depending on different viral construction. This has to be confirmed by further experiments. Experiments are ongoing to resolve this issue.

Bioreactor Run of Serum-free 293SF-3F6 Cell Culture

Figure 4A:
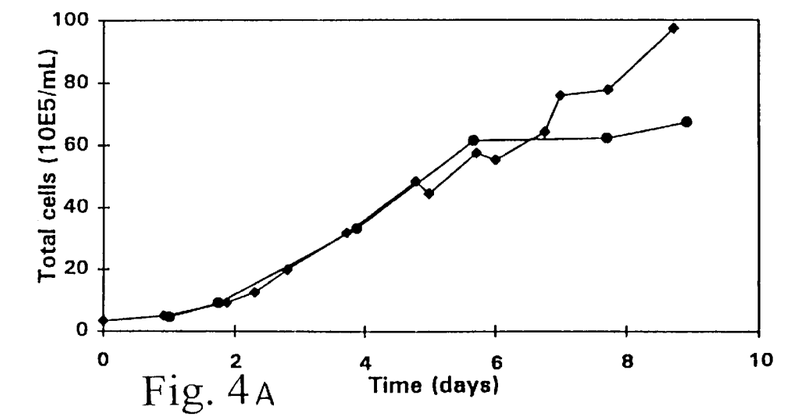
FIG. 4A illustrates growth curves of serum-free 293SF-3F6 batch cultures in 2.8 L bioreactor (diamonds) and 600 mL culture in 2000 mL shake flask (circles)
Figure 4B:
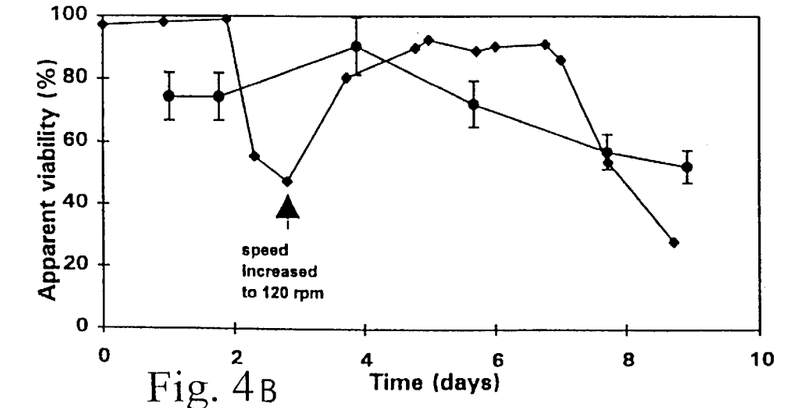
FIG. 4B illustrates culture viability of serum-free 293SF-3F6 batch cultures in 2.8 L bioreactor (diamonds) and 600 mL culture in 2000 mL shake flask (circles)
Figure 4C:
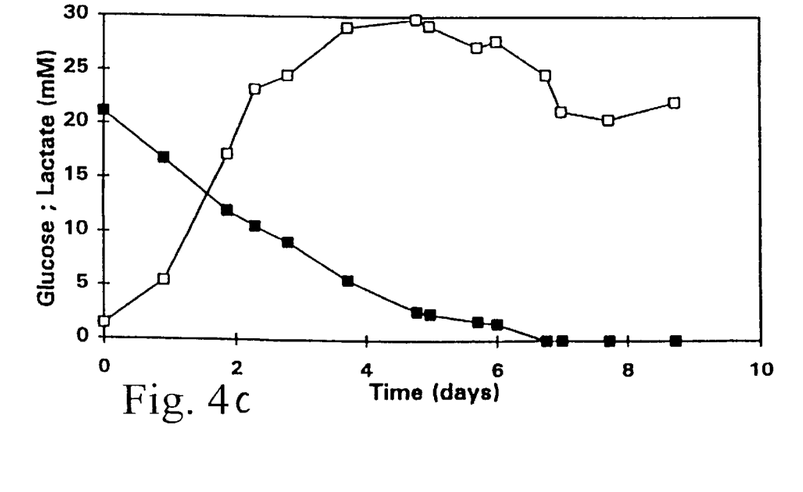
FIG. 4C illustrates glucose (solid squares) and lactate (open squares) concentrations during bioreactor run.

The 293SF-3F6 cell growth in CLC-SFM in the 3L-bioreactor was comparable to shake flask controls as shown in FIG. 4. The doubling time calculated between cell densities ranging from 4.5×10$^5$ cells/mL to 3×10$^6$ cells/mL was 24 hours. The maximum cell density was 9.7×10$^6$ cells/mL in the bioreactor as compared to 6.7×10$^6$ cells/mL for shake flask controls. The agitation provided by the helical ribbon impeller in the bioreactor allowed the cells to reach almost 10$^7$ cells/mL without cell aggregation. Apparent viability (FIG. 4b) decreased rapidly on the third day of culture in the bioreactor since stronger manual agitation was necessary to break down large and compact cell aggregates (approx. 200 cells per aggregate) prior to microscopic count with erythrosin B. This apparent cell viability decrease did not correlate with the culture viability at that point but was in fact caused by the strong agitation necessary for cell counting. Increasing agitation speed from 100 to 120 rpm after 60 hours of culture showed that cell aggregation was reversible and allowed almost completely aggregate-free suspension culture of 293SF-3F6 cells. The bioreactor culture viability was maintained higher than 90% until glucose, the main limiting nutrient, was depleted after 160 hours of culture. Culture viabilities appeared lower in shake flask controls than in the bioreactor since bigger aggregates were observed in the first ones necessitating stronger agitation for cell counts. During the growth phase, glucose uptake rate was constant and maximum from inoculation until day 5 when glucose concentration decreased below 2 mM. From day 5 to day 7, glucose was consumed at a lower rate corresponding to a linear growth curve while lactate began to be consumed (FIG. 4c). During the same period, lactate concentration decreased from 30 mM to 22 mM. In fact, 2 mM glucose and 8 mM lactate were consumed until glucose was completely exhausted at day 7. This suggests that the overall lactate/glucose yield for glucose concentration lower than 2 mM is decreased leading to lower lactate production. We previously demonstrated (Nadeau, I et al. 1996 Biotech. Bioeng. 51:613–623) that high lactate concentration may be disadvantageous to r-protein production with the AdV/293 expression system. Using on-line monitoring for glucose in order to maintain constant and low glucose concentration would potentially improve adenovirus titer in such conditions.

Bioreactor Run of Infected Serum-free 293SF-3F6 Cell Culture

Figure 5:
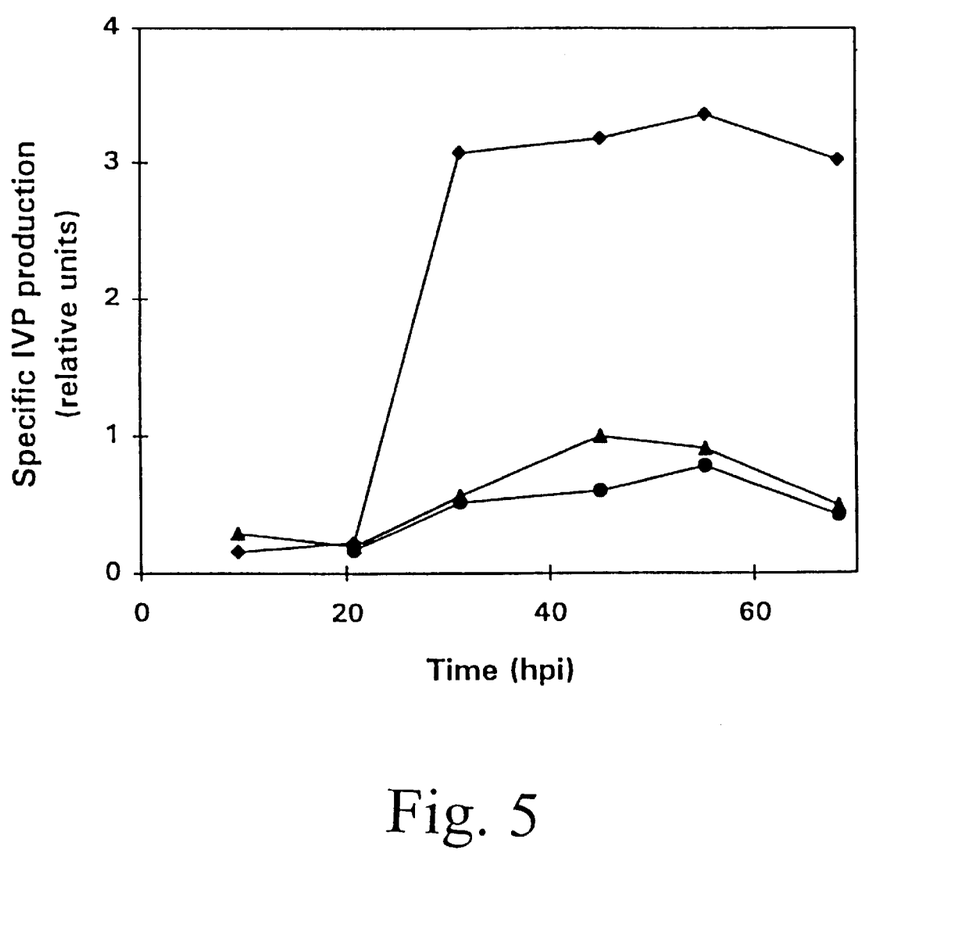
FIG. 5 illustrates comparative specific infectious Ad5 CMV-LacZ viral particles (IVPs) in bioreactor and in shake flasks relative to IVPs produced in 35 mL low-cell density cultures in 125 mL shake flasks by 293S cells in complete CFDMEM at $8\times10^5$ cells per mL (triangles)

Production of infectious adenoviral particles was estimated by infecting 293S cells in wells as described in Materials and Methods. The values are relative to infectious adenoviral particle counts per cell at 45 hpi for low-density 293S cell culture in shake flask where the medium was replaced at the time of infection only. This control corresponds to the maximum production of IVPs usually produced in small-scale suspension conditions. Relative IVPs per cell are reported in FIG. 5. 293SF-3F6 cells in CLC-SFM were infected at a cell density of $1.6 \times 10^6$ cells per mL in 125 mL shake flasks (circles) and in a 2.8 L bioreactor (diamonds). Cell density of 293S shake flask control was $8 \times 10^5$ cells/mL while the 293SF-3F6 cell density in bioreactor and shake flask control was increased up to $1.6 \times 10^6$ cells/mL. Specific IVPs obtained in bioreactor at high cell density is about 3 fold higher than the one obtained with the 293S control (FIG. 5). The culture viability in the bioreactor was comparable to both shake flask controls until 48 hpi with 50±10% and went down to 40% at 70 hpi as compared to 10% for the controls. The 293SF-3F6 shake flask control indicates that higher cell density in shake flask does not sustain such a high specific AdV production and that is thought to be mainly related to medium acidification.

Stable cell line derived from 293S cells secreting the soluble epidermal growth factor receptor was used to select the most promising serum-free medium tested and also commercially available. A successful adaptation of the 293 human embryonic kidney cell line to serum-free medium and suspension culture was performed.

It was also demonstrated that adenoviral particles could be produced in suspension culture when an adequate serum-free formulation was used. The CLC-SFM used to grow 293SF-3F6 cells allowed the production of adenoviral particles to levels comparable to those obtained with the standard serum-containing 293S suspension culture.

A 3L-scale bioreactor culture of 293SF-3F6 cells in serum-free medium was demonstrated. The maximum cell density obtained was about $1 \times 10^7$ cells/mL which represents a 100% increase of the cell density obtained for parental 293S cells in serum-containing medium. Additionally, the controlled environment in bioreactor allowed an AdV yield improvement up to three fold as compared to shake flask cultures.

Currently, in the Applicants' laboratory, AdVs are readily produced in serum-containing culture of 293S cells in 20 L-bioreactor. However, in absence of serum, 293SF-3F6 cells may be more sensitive to shear stress than 293S cells. Moreover, infected cells are even more fragile than uninfected cells and this is particularly true in serum-free conditions. Bioreactor design is of first importance for serum-free mammalian cell culture and maybe even more for infected cells. Adenoviral production was possible in serum-free conditions at least up to 3 L suspension culture in bioreactor. Studies are presently conducted to grow 293SF-3F6 cells in 20 L bioreactor to face the needs for large quantities of viral particles used in gene therapy preclinical studies. In parallel, increasing the cell density at infection close to the maximum cell density reached in batch would be a major progress.

Improvement of serum-free formulation to support growth and production at large scale is our current focus. However, in order to test different parameters with the objective of improving infected cell viability and AdV productivity in serum-free suspension culture, precise, fast and reproducible quantification is needed. Therefore the choice of the AdV model is critical. The green fluorescent protein, from the Jellyfish *Acquorea victoria,* is presently being used in our laboratory as a reporter gene (Côté, J et al. 1997. Biotechnol. Prog. 13:709–714) and appears to be a promising model for AdV production bioprocess development.

The present invention will be more readily understood by referring to the following examples which are given to illustrate the invention rather than to limit its scope.

EXAMPLE I

Green Fluorescent Protein as Reporter Gene for Adenovirus Production in Serum-free 293SF Suspension Culture The red-shifted S65T mutant green fluorescent protein (GFP) was used to compare the adenovirus (Ad) production and post-infection survival of 293SF and 293S cells in serum-free and serum-containing flask cultures, respectively. The fluorescent vector permitted the quantification of both the number of infected cells and the infectious virus content of the cultures by flow cytometry in a simple, fast, sensitive, and reliable way. Infected cultures showed the co-existence of two populations of fluorescent cells, high-fluorescence cells (HFCs) and low-fluorescence cells (LFCs), in sizes that varied in time. The gradual increase in the number of LFCs at the expense of HFCs correlated well with the increase in the number of dead cells. This relationship could be used for the continuous measure of a culture's viability with the appropriate on-line instrumentation. The post-infection death rate of infected 293SF cells was higher than that of infected 293S cells, but the level of GFP fluorescence in live, highly fluorescent cells was similar in the two infected cell lines. The number of infectious viral particles (IVPs) was quantified in less than 24 h by an assay infection of 293S cells in wells with viral particles extracted from the culture samples, and the results were more reproducible (±5% variation for triplicates) than those of conventional plaque assay titrations or end-point dilutions. The live cell-specific IVP concentrations were for most experiments similar, indicating again that the difference between the two cell lines was their unequal post-infection viabilities, not the virus production in the infected live cells. The absence of serum did not affect the virus production in live 293SF cells in a visible way.

Ad-GFP

The recombinant adenovirus was constructed as the previously described Ad5 CMV-LacZ (Acsadi, G. et al. 1994. Hum. Mol. Genet. 3:579–584), but with some modifications, including the replacement of the LacZ gene by the S65T GFP mutant gene. This variant produced the S65T mutant GFP with an increased emission signal intensity detectable in single cells, either by fluorescent microscopy or FCM.

Infection and Sampling

The infection experiments were performed in 125-mL shake flasks at working volumes of 35 mL. The cells were maintained in exponential growth phase, and then centrifuged and resuspended in fresh medium prior to infection. Infections were done at $1 \times 10^6$ cells/mL with a multiplicity of infection (MOI) of 10 IVPs per cell. Static controls were prepared by transferring infected cells from some shake flasks to 25-cm$^2$ T-flasks. The infected cultures were incubated at 37° C. in an atmosphere of 5% $CO_2$ (Forma Scientific incubator). Aseptic samples of 1.3 mL were taken twice daily. 300 µL were used for haemacytometer cell counts with erythrosin B exclusion. 500 µL were transferred in 15-mL sterile tubes. 500 µL were centrifuged at 500 g for 2 min (Eppendorf Savant Centrifuge). The total-suspension samples and centrifugation supernatants were kept at −80° C. The centrifugation pellets were resuspended by gentle manual shaking, and 500 µL of cold phosphate-buffer saline (PBS) were added. The cells were then fixed for FCM in the following way: 500 µL of PBS containing 4% paraformaldehyde were added to the suspension drop by drop under constant, gentle agitation to prevent cell aggregation; the cells were incubated at 4° C. for 30 min, centrifuged, and washed once with cold PBS; the cells were then resuspended in 500 µL of cold PBS and assayed by FCM. We assayed the same samples immediately after fixation and once a day until the third day. The fluorescence decreased by 30% during the first 12 h and then remained stable for at least 3 days at 4° C. We found that accumulating fixed-cell samples at 4° C. and assaying them all at the same time gave the best results.

Analysis by FCM

The fixed-cell suspensions were analyzed with a Profile II flow cytometer (Coulter Electronics, Hialeah, Fla., U.S.A.) equipped with a 15-mW argon-ion laser, as described by Mosser et al. (Mosser D. D. et al. 1997. BioTechniques 22:150–161). The fluorescence intensity was an indicator of the GFP level produced over the infection period (GFP-positive cells). The GFP signal distribution represents the number of IVPs per cell, or MOI, which extends over almost one log range.

Infectious-viral Titer by Assay Infection of 293S cells in Wells

A method was developed to measure the number of mature, infectious virions (IVPs) in a sample by taking into account virus penetration as well as viral gene expression. Each well of a 24-well plate was seeded with $1.3 \times 10^6$ 293S cells. Some trials were also done in 6-well plates. To each well, 2 mL CFDMEM containing 5% BCS were added. The frozen total-suspension samples of the shake-flask and T-flask cultures were submitted to 3 freeze-thaw cycles to release the Ad-GFP from the cells. The frozen culture supernatants of the cultures were also thawed (once) and then diluted in fresh serum-containing medium. To each well were added 5 to 50 µL of diluted samples. After an incubation at 37° C. and 7% $CO_2$, the cells were harvested (1 mL from each well) at 16 to 18 hpi, fixed with paraformaldehyde as described above, and analyzed by FCM immediately. This short infection period allowed the virus to enter the cells and express the GFP at a level detectable by FCM. At 18 hpi there is no viral amplification (mature virions), but viral genes are expressed and can be detected. Some samples were observed under the fluorescence microscope. FCs were visible this way, but at least twice as many could be detected in the same samples by the more sensitive FCM.

The percentage of fluorescent cells (FCs) increased linearly with the amount of virus added in wells in which no more than 50% of all cells were infected. Each FC received at least one IVP, and if a Poisson distribution is assumed, almost all the FCs contained only 1 IVP when less than 50% of the total cell population was infected. The viral titers are therefore reported only for wells containing no more than 50% FCs. They were calculated the following way:

$$(1) \quad \frac{\% \text{ FCs} \cdot \text{Dilution} \cdot X}{\text{Sample volume}} = \text{IVPs per mL}$$

$$(2) \quad \frac{\text{IVPs per mL}}{\text{Cell density}} = \text{IVPs per cell}$$

where % FCs is the percentage of fluorescent cells, and X is the number of cells per well. For this assay infection, we considered the percentage of fluorescent cells only, not the intensity of fluorescence in fluorescent cells, since only one IVP was expected to enter into a single cell in most instances.

GFP Expression by Cells after Infection

Figure 6:
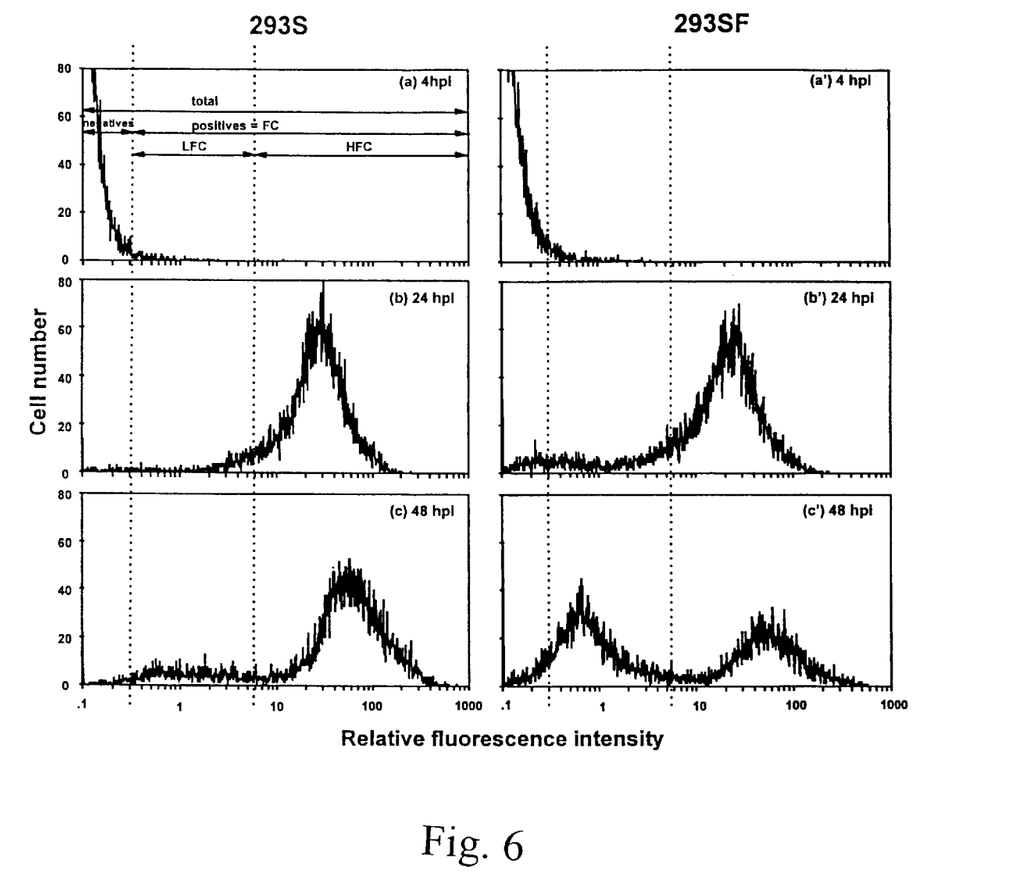
FIG. 6 illustrates flow-cytometric analysis of 293 cells infected with Ad-GFP at an MOI of 10 IVPs per cell at a) 4 hpi (negative control); b) 293S cells at 24 hpi, where 98% of positive cells are highly fluorescent; and c) 293SF cells at 48 hpi, when cell viability was around 50%.
Figure 7:
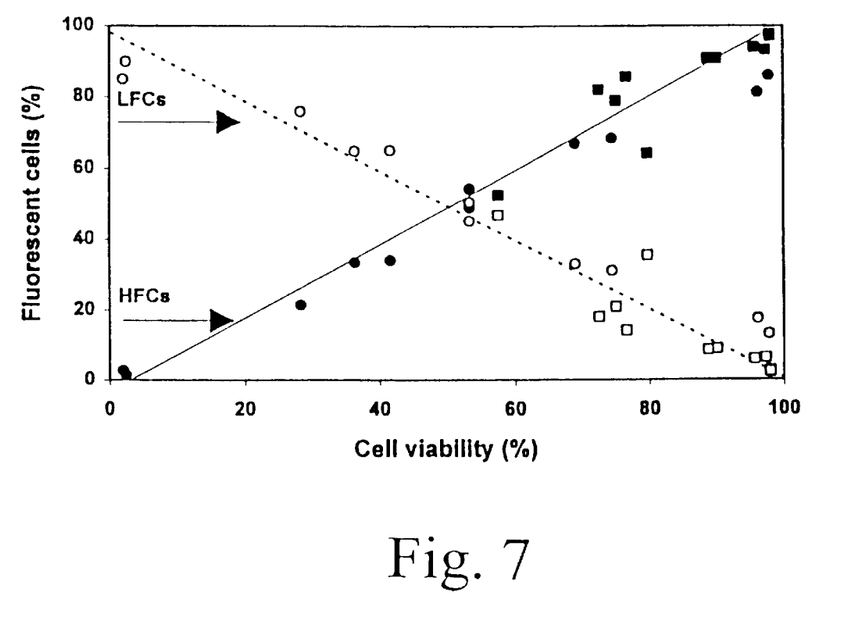
FIG. 7 illustrates faction of fluorescent cells as a function of cell viability in all experiments.

FIG. 6 shows flow-cytometric profiles of 293 cells during infection. The negative control (FIG. 6a) corresponds to cells that have just been infected by Ad-GFP (less than 4 hpi). The high-fluorescence-cell (HFC) peak on FIG. 6b was observed with 293S cells at 24 hpi. This intensity of signal is close to the maximum observed under these conditions for both cell lines. FIG. 6c shows a population of 293SF cells at 48 hpi, when the cell viability was around 50%. Two peaks appear, one HFC peak equivalent to that of FIG. 6b, and a low-fluorescence-cell (LFC) peak of cells of inferior GFP content and of mean intensity almost two orders of magnitude lower than that of the HFC peak. Samples taken at other times show correspondingly intermediate ratios of HFCs to LFCs. In all samples, a linear correlation ($r^2=0.95$) was observed between the proportion of HFCs and the fraction of live cells determined by haemacytometer counts (FIG. 7). 293S cells (squares) and 293SF cells (circles) in T-flasks and shake-flasks. Open symbols: low-fluorescence cells; closed symbols: high-fluorescence cells. FIG. 7 also shows an inverse linear relationship ($r^2=0.94$) between the proportion of LFCs and the fraction of live cells. Therefore, the LFC peak is proportional to the population of dead cells, whereas the HFC peak represents the fraction of live cells. Presumably, a fraction of the GFP content of the live infected cells leaked at death, resulting in dead cells of lower fluorescence. However, the dead-cell fluorescence signal did not reach the values of the negative control. The mean signal decreased faster in 293SF cells than in 293S cells. The correspondence between the fraction of HFCs and the percentage of live cells could be used as a tool to determine the viability of an Ad-GFP infected culture. With the appropriate equipment, this could be done on-line, which is a net advantage over haemacytometer counts.

Post-infection Cell Survival and Fluorescence

Figure 8A:
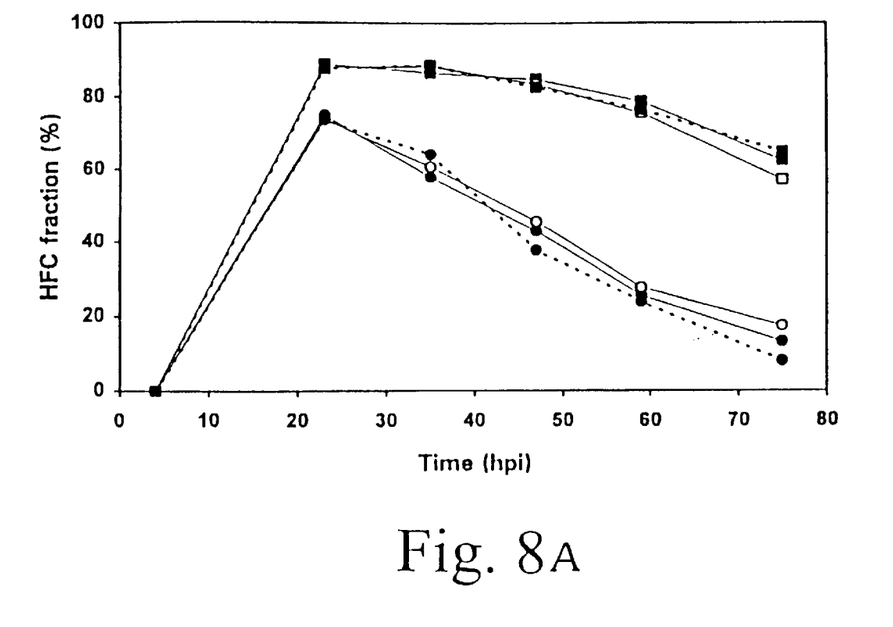
FIG. 8 illustrates time course of a) high-fluorescence-cell fraction and b) low-fluorescence-cell fraction after infection in all experiments.
Figure 8B:
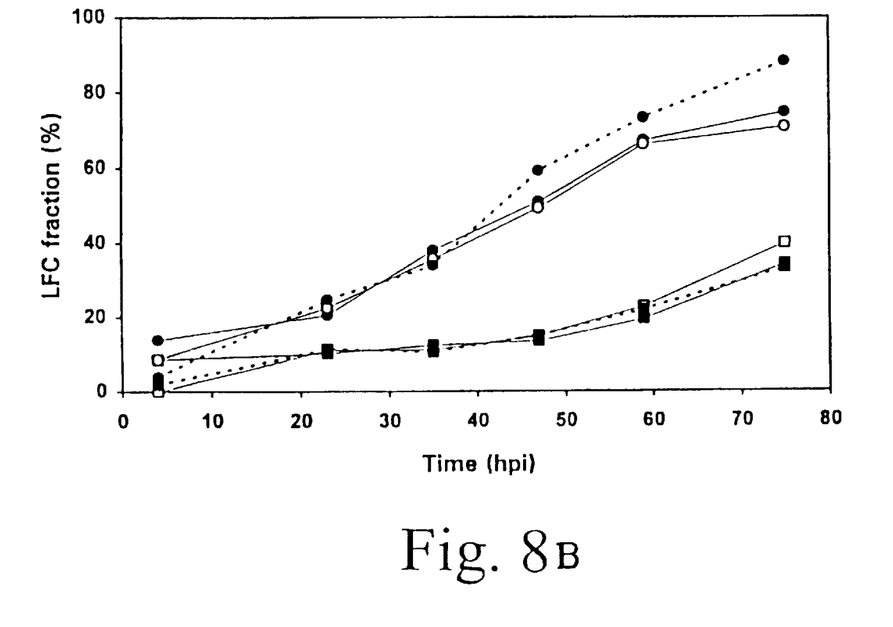

FIG. 8a shows the changes in the fraction of HFCs after infection in shake-flask and T-flask cultures, whereas the changes in the fraction of LFCs are shown on FIG. 8b. 293S cells (squares) and 293SF cells (circles) in T-flasks (dashed lines) and shake-flasks (solid lines). Open and closed symbols are duplicates. Between 24 and 75 hpi, the two quantities may be interpreted as the fractions of live cells and dead cells, respectively. Values before 4 hpi are not representative of cell state, since the GFP was not produced or detectable at that time. The death rate of 293S cells was substantially lower than that of 293SF cells over the 3-day infected period. The viability of 99% at infection decreased after 3 days to about 70% for 293S cells and 15% for 293SF cells. Cell viability profiles were similar for infected cells in static and agitated cultures. This indicates that cell death was more related to the infection itself than to any stress caused by agitation, especially in serum-free conditions.

Figure 9A:
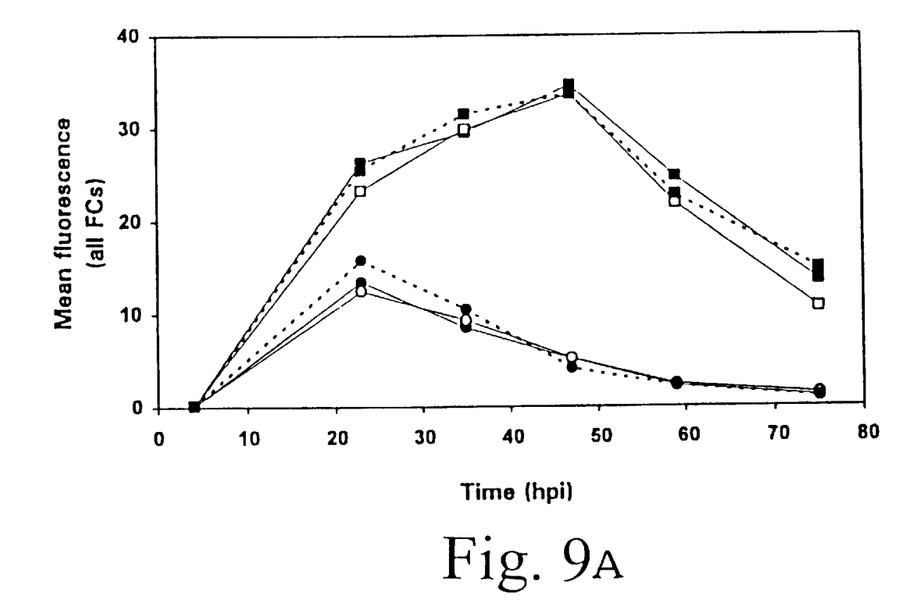
FIG. 9 illustrates mean fluorescence of a) all fluorescent cells and b) high-fluorescence cells.
Figure 9B:
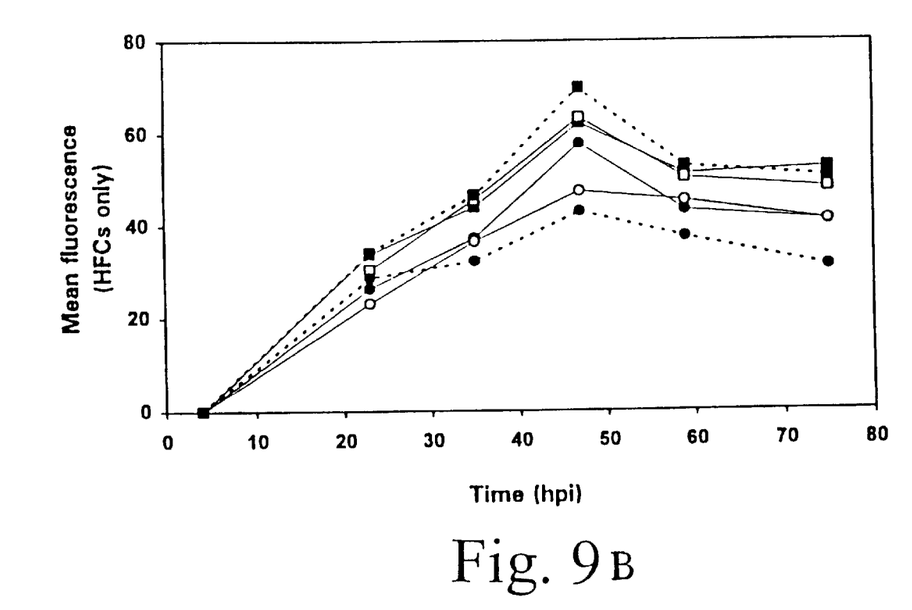

FIG. 9a shows that the mean fluorescence of all fluorescent 293S cells increased rapidly in the first 24 hpi, increased more slowly between 24 and 48 hpi, and decreased afterwards, whereas the mean fluorescence of all fluorescent 293SF cells peaked at 24 hpi, after which it decreased. 293S cells (squares) and 293SF cells (circles) in T-flasks (dashed lines) and shake-flasks (solid lines). Open and closed symbols are duplicates. In both cultures, the decline in mean fluorescence owed to the gradual increase in number of low-fluorescence dead cells. When only the mean fluorescence of infected live cells is considered (FIG. 9b), it can be seen that similar amounts of GFP were produced at similar rates in all conditions by both cell lines, although 293SF were on average slightly less productive in HFCs.

Production of IVPs

Figure 10A:
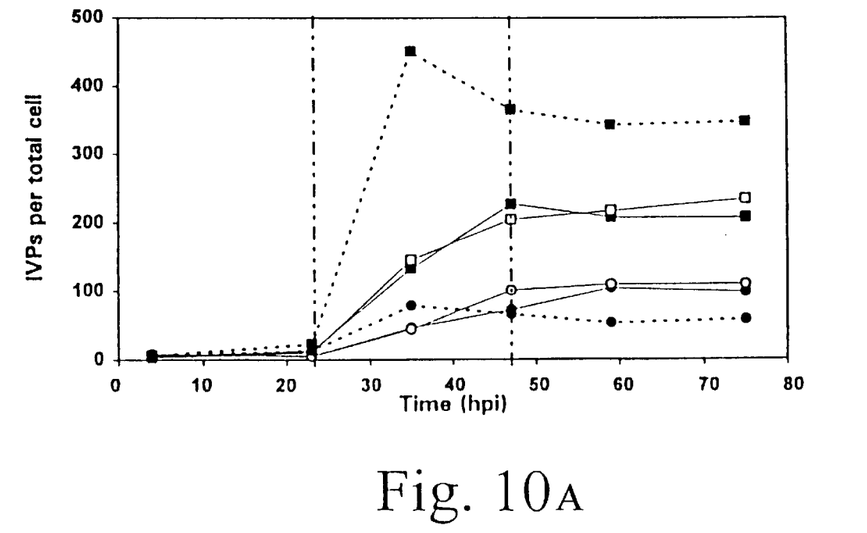
FIG. 10 illustrates specific total-suspension infectious viral particles (IVPs) measured by assay infections in wells.
Figure 10B:
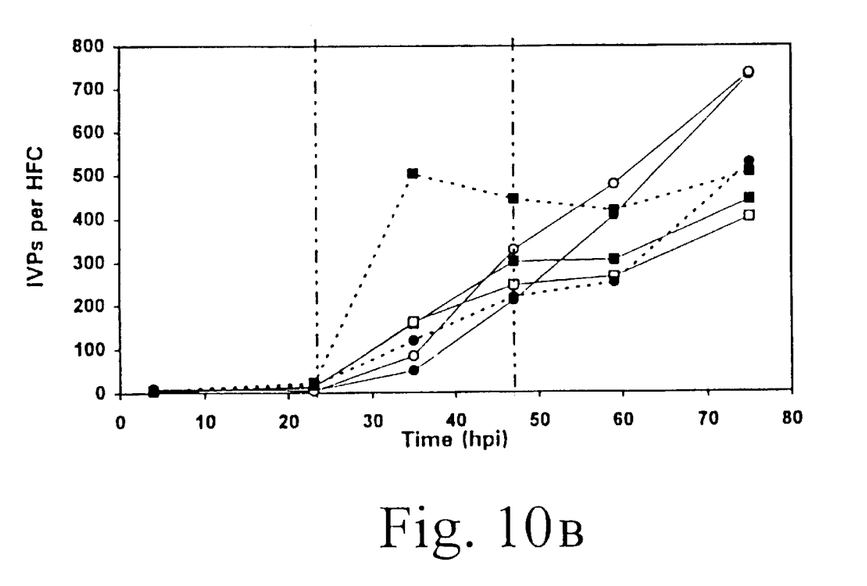

The assay infections in 24-well plates showed standard deviations of less than 5%. The highest final Ad-GFP titer, 350 IVPs/($10^6$ total cells), was obtained with total-suspension 293S cells in 5% BCS in T-flasks (FIG. 10a). 293S cells (squares) and 293SF cells (circles) in T-flasks (dashed lines) and shake-flasks (solid lines). Open and closed symbols are duplicates. In the shake-flask samples, 200 IVPs/($10^6$ total cells) were measured with 293S cells in BCS, whereas 293SF cells in SFM yielded about 100 IVPs/($10^6$ total cells). But the live cell-specific IVP concentrations (FIG. 10b) were for most experiments similar until 48 hpi, indicating here also that the difference between the two cell lines was their unequal viabilities, not the virus production in the infected live cells. The absence of serum did not affect the latter parameter in 293SF cells in a discernible way; as long as they were alive, infected 293SF cells produced infectious virions as well as 293S cells. Since the Ad-GFP titer at 24 hpi was still about equal to the MOI at infection (10 IVPs per cell), the subsequently produced IVPs came from cells that were alive after 24 hpi; the dead cells did not produce infectious viral particles. After 48 hpi, the apparent increase in the live cell-specific Ad-GFP concentration owed to the gradual decrease in the number of live cells as they died, rather than to a real viral production, since the total population-specific titer remained constant during that time (FIG. 10a).

In culture supernatants alone, the amount of virus released ranged from 1% to 10% to 20% of the total-suspension Ad-GFP, even in the late-stage samples with a dead-cell fraction as high as 90%. The quantity nevertheless correlated well with the cell death that followed the maximal Ad-GFP content at 48 hpi. The decrease in cell viability ranged from 13% to 28% in the period between 48 and 75 hpi (see FIG. 8), which is close to the 10% to 20% release of viral particles.

GFP monitoring by FCM is a useful method for the analysis of an infected culture's virus production that avoids the multiple steps usually needed to label a product of interest. The fact that a reproducible viral quantification can be quickly done is of value for process study.

The level of GFP in live highly fluorescent cells was similar in serum-containing and serum-free cultures of 293S and 293SF cells, respectively, infected with the adenovirus. The culture mean fluorescence decreased in a manner that correlated well with the apparition of a population of low-fluorescence dead cells. These findings could be used for the continuous assessment of a culture's viability with the appropriate on-line instrumentation.

Live infected 293SF cells produced the same amount of recombinant protein and infectious recombinant adenovirus as live infected 293S cells in suspension culture, but the post-infection survival of 293SF cells was shorter. We are presently conducting studies to improve the cell viability following infection in serum-free conditions.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. An immortalized animal cell line for the expression of adenoviral vectors, said cell line being viable in a serum-free medium, and wherein said cell line has the identifying characteristics of cell line 293SF-3F6 having ATCC accession number ATCC CRL-12585.

2. The cell line of claim 1, wherein said animal is a mammal.

3. The cell line of claim 2, wherein said mammal is human.

4. The cell line of claim 3, wherein said human cell line is a human embryonic kidney cell line.

5. A method of serum-free production of recombinant proteins, which comprises the steps of:
   a) transfecting a serum-free cell line of claim 1, 2, 3 or 4 with a cDNA coding for a recombinant protein to obtain transformants;
   b) isolating a stable transformant of step a);
   c) cultivating said isolated transformant of step b) in suspension in a serum-free medium to produce said recombinant proteins; and
   d) isolating said recombinant proteins of step c).

6. The method of claim 5, wherein said recombinant protein is selected from the group consisting of cytokines, G-protein coupled receptors, hormones and enzymes.

7. The method of claim 5, wherein step b) is effected using a selection marker.

8. A method of serum-free production of recombinant adenoviral vectors, which comprises the steps of:
   a) transforming a serum-free cell line of claim 1, 2, 3, or 4, which is complementing defective of an adenoviral vector, with a recombinant adenoviral vector comprising a promoter operatively linked upstream to a marker gene and/or a therapeutic gene sequence relative to the direction of transcription in an adenoviral vector, wherein said promoter is controlling transcription of said marker gene and/or said therapeutic gene, wherein said cell line is complementing said recombinant adenoviral vector;
   b) isolating a stable cell line of step a) using said marker; and
   c) cultivating said isolated cells of step b) in suspension in a serum-free medium to produce said recombinant adenoviral vector.

9. The method of claim 8, wherein said marker is green fluorescent protein, β-galactosidase or luciferase.

10. The method of claim 9, wherein said vector of step a) is Ad5 CMV-LacZ wherein LacZ gene is replaced by S65T GFP mutant gene, thereby having an increased emission signal intensity detectable in single cells by fluorescent microscopy or FCM.

11. A method of obtaining cell lines for the expression of recombinant proteins and/or adenoviral vectors and which are viable in a serum-free medium, which comprises the steps of:
   a) incubating immortalized cells secreting recombinant proteins and/or adenoviral vectors in a serum-free medium and incubating parental cells in a serum-containing medium;
   b) gradually adapting the immortalized serum-free cells of step a) to a low-calcium version of said serum-free medium, thereby reducing cell aggregation; and
   c) screening and cloning cells of step b) based on their ability to grow in a serum-free medium at a rate and an extent comparable to those of said parental cells in serum-containing medium as single cells.

12. The method of claim 11, wherein the cells of step c) are screened for their ability to grow at the highest specific cell growth rate and cell density while forming least and smallest cell aggregates in shake flask suspension culture.

* * * * *